US008273580B2

(12) United States Patent
Yamamoto et al.

(10) Patent No.: US 8,273,580 B2
(45) Date of Patent: *Sep. 25, 2012

(54) METHOD OF MEASURING THE CONCENTRATION OF A GLYCOSAMINOGLYCAN ANTICOAGULANT

(75) Inventors: Ralph Yamamoto, Naperville, IL (US); Yumi Kim, Woodridge, IL (US)

(73) Assignee: Active BioMaterials, LLC, Los Angeles, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/176,655

(22) Filed: Jul. 5, 2011

(65) Prior Publication Data
US 2012/0009686 A1 Jan. 12, 2012

Related U.S. Application Data (63) Continuation of application No. 12/179,434, filed on Jul. 24, 2008, now Pat. No. 8,003,402.

(60) Provisional application No. 60/951,504, filed on Jul. 24, 2007.

(51) Int. Cl.
G01N 21/75 (2006.01)
G01N 21/77 (2006.01)
G01N 33/86 (2006.01)

(52) U.S. Cl. ............ 436/164; 436/18; 436/69; 436/166; 436/174; 435/13; 134/1; 134/42

(58) Field of Classification Search ................ 436/8, 18, 436/63, 69, 164, 166, 174; 422/73, 82.05, 422/82.09; 435/13; 134/1, 42
See application file for complete search history.

(56) References Cited

U.S. PATENT DOCUMENTS

| 5,284,155 | A | 2/1994 | Treadwell et al. |
| 5,310,646 | A | 5/1994 | Whitley |
| 6,190,875 | B1 | 2/2001 | Ben-Artzi et al. |
| 8,003,402 | B2 * | 8/2011 | Yamamoto et al. ........... 436/164 |
| 2002/0009782 | A1 * | 1/2002 | Miron ............................ 435/84 |
| 2003/0203385 | A1 | 10/2003 | Venkataraman et al. |
| 2005/0238536 | A1 * | 10/2005 | Striepeke et al. ............ 422/68.1 |

OTHER PUBLICATIONS

Arixtra® package insert, GlaxoSmithKline (Oct. 2005).
Barbosa et al., *Glycobiology*, 13(9), 647-653 (2003).
Blyscan™ "Sulfated Glycosaminoglycan Assay," www.biocolor.co.uk,© Biocolor Ltd. (1994).
De Lima et al., Clin. Chim. Acta, 378, 206-215 (Mar.2007).
Fragmin® Package insert, Pfizer Inc. (Aug. 2006)
Gandra et al., *Glycobiology*, 10(12), 1333-1340 (2000).
Guimarães et al., *Biochim Biophys Acta*, 1335, 161-172 (1997).
Lovenox® package insert, Aventis Pharmaceuticals Inc. (Nov. 2005).
Milovic et al., *PNAS*, 103(36), 13374-13379 (Sep. 5, 2006).
Rydberg et al., *American Family Physician*, 59(6), 1607-1612 (Mar. 15, 1999).
Sabiston et al., *Analytical Biochemistry*, 149, 543-548 (1985).
Toyoshima et al., *J. Biol. Chem.*, 274(34), 24153-24160 (1999).

* cited by examiner

*Primary Examiner* — Maureen Wallenhorst
(74) *Attorney, Agent, or Firm* — Leydig, Voit & Mayer, Ltd.

(57) ABSTRACT

The invention provides an accurate, economical, automatable, high throughput method for the determination of the concentration of glycosaminoglycan anticoagulants, including low molecular weight heparin (LMWH) anticoagulants, in aqueous solutions. A method for cleaning a unit of manufacturing equipment used in the preparation of a LMWH to obtain an acceptable residual concentration of LMWH is further provided.

10 Claims, 9 Drawing Sheets

First Set of Experiments

FIG. 8B

Second Set of Experiments

METHOD OF MEASURING THE CONCENTRATION OF A GLYCOSAMINOGLYCAN ANTICOAGULANT

CROSS-REFERENCE TO RELATED APPLICATIONS

This application is a continuation of U.S. patent application Ser. No. 12/179,434, filed Jul. 24, 2008, now U.S. Pat. No. 8,003,402, issued on Aug. 23, 2011, which claims priority to U.S. Provisional Patent Application 60/951,504, filed Jul. 24, 2007, the content of each application being incorporated by reference.

BACKGROUND OF THE INVENTION

Low-molecular-weight heparins ("LMWHs") are an important class of antithrombotic compounds. LMWHs are safe and effective for the prevention and treatment of venous thromboembolism and several are approved for these uses in Europe and North America. The LMWHs have the advantage that they can be given subcutaneously and do not require APTT monitoring. Thus, LMWHs permit the outpatient treatment of conditions such as deep vein thrombosis and pulmonary embolism that previously required hospitalization.

LMWHs are glycosaminoglycans consisting of chains of alternating residues of D-glucosamine and one of the two uronic acids: uronic acid, either glucuronic acid or iduronic acid. While unfractionated heparin is a heterogeneous mixture of polysaccharide chains ranging in molecular weight from about 3,000 to 30,000, LMWHs—which are often produced by a controlled enzymatic or chemical depolymerization of heparin—have mean molecular weights of about 5,000. All heparins derive their anticoagulant activity from activating antithrombin (previously known as antithrombin III). This activation is mediated by a unique pentasaccharide sequence that is randomly distributed along the heparin chains. About one third of the chains of unfractionated heparin, but only 15 to 25 percent of the chains of LMWHs, contain the pentasaccharide sequence.

There are differences between unfractionated heparin and LMWHs relating to their relative inhibitory activity against factor Xa and thrombin. Any pentasaccharide-containing heparin chain can inhibit the action of factor Xa simply by binding to antithrombin. However, to inactivate thrombin, heparin must form a ternary complex, by binding to both antithrombin and thrombin. Such complexes are only formed by pentasaccharide-containing heparin. Since fewer than half of LMWHs molecules are of sufficient length to bind to both antithrombin and thrombin, LMWHs have less activity than that against thrombin. On the other hand, LMWH have greater activity against factor Xa. The relative importance of inhibition of factor Xa and inhibition of thrombin in mediating an antithrombotic effect varies with the clinical setting, but there is evidence that both are necessary. Accordingly, the LMWHs have increasingly been used for the therapy of conditions with an elevated risk of blot clots.

The LMWHs are typically formulated for clinical use in aqueous solutions. Because of their potent anti-coagulant activity it is necessary to accurately monitor LMWHs' concentrations during their formulation and packaging into pharmaceuticals. Further, the ability to measure the concentration of an experimental sample is fundamental to any research and development program seeking to invent new glycosaminoglycan anticoagulants.

Prior to the current invention, such measurements have required the use of UV light absorption and refractive index-based techniques. However, the use of UV absorption is complicated by the fact that some LMWHs produce only a very weak UV signal that is nearly undetectable. In addition, UV methods require large amounts of test material making them impractical, especially when sample volumes are limiting. Further, UV absorption is not readily adaptable to the rapid, high-throughput quantitative assay format. Similarly, refractive index-based techniques lack specificity and can result in artificially high results. Such inaccuracies are particularly undesirable when measuring drug levels.

Thus, there remains a need for methods that can measure the concentration of glycosaminoglycan anticoagulants, such as LMWHs, in solution which are accurately quantitative, quick, easily performed, and amenable to high throughput.

BRIEF SUMMARY OF THE INVENTION

The invention provides a method of measuring the concentration of a test glycosaminoglycan anticoagulant in an aqueous solution comprising:
(a) assaying a sample containing the test glycosaminoglycan anticoagulant comprising
  (i) providing a sample containing the test glycosaminoglycan anticoagulant;
  (ii) reacting the sample with 1,9-dimethyl-methylene blue; and
  (iii) determining the absorbance of the sample after reaction with 1,9-dimethyl-methylene blue;
(b) determining the concentration of the sample containing the test glycosaminoglycan anticoagulant by comparing its absorbance with the absorbances of a plurality of samples of control glycosaminoglycan anticoagulant in aqueous solutions of known concentration.

In another embodiment, the invention provides a method of measuring the concentration of a test glycosaminoglycan anticoagulant in an aqueous solution comprising:
(a) assaying a plurality of samples containing control glycosaminoglycan anticoagulants in aqueous solutions of known concentration comprising
  (i) providing a plurality of samples of a control glycosaminoglycan anticoagulant in aqueous solutions of known concentration,
  (ii) reacting the samples of the control glycosaminoglycan with 1,9-dimethyl-methylene blue,
  (iii) determining the absorbance of the samples of the control glycosaminoglycan after their reaction with 1,9-dimethyl-methylene blue;
(b) assaying a sample containing the test glycosaminoglycan anticoagulant of unknown concentration in an aqueous solution comprising
  (i) providing a sample containing the test glycosaminoglycan anticoagulant of unknown concentration,
  (ii) reacting the sample of unknown concentration with 1,9-dimethyl-methylene blue,
  (iii) determining the absorbance of the sample of unknown concentration after reaction with 1,9-dimethyl-methylene blue;
(c) determining the concentration of the sample containing the test glycosaminoglycan anticoagulant of unknown concentration by comparing its absorbance with the absorbances of the standard curve samples of control glycosaminoglycan anticoagulant in an aqueous solutions of known concentration.

In a further embodiment, the invention provides a method for cleaning a unit of manufacturing equipment used in the preparation of a low molecular weight heparin (LMWH) to obtain an acceptable residual concentration of LMWH comprising:
   (a) subjecting the unit of manufacturing equipment to a cleaning protocol;
   (b) obtaining the absorbance of a sample obtained from the manufacturing equipment comprising: (i) collecting a sample from the manufacturing equipment; (ii) reacting the sample with 1,9-dimethyl-methylene blue; and (iii) determining the absorbance of the sample reacted with 1,9 dimethyl-methylene blue;
   (c) determining the concentration of LMWH in the sample obtained from the manufacturing equipment by comparing its absorbance with the absorbances of a plurality of samples of control LMWH in aqueous solutions of known concentrations; and
   (d) optionally repeating steps (a)-(d) until the concentration of LMWH in the sample obtained from the manufacturing equipment is less than an acceptable residual concentration of LMWH.

The present invention is also directed to a method for cleaning a unit of manufacturing equipment used in the preparation of a low molecular weight heparin (LMWH) to obtain an acceptable residual concentration of LMWH comprising:
   (a) subjecting the unit of manufacturing equipment to a cleaning protocol;
   (b) obtaining the absorbance of a sample obtained from the manufacturing equipment comprising: (i) collecting a sample from the manufacturing equipment; (ii) reacting the sample with 1,9-dimethyl-methylene blue; and (iii) determining the absorbance of the sample reacted with 1,9 dimethyl-methylene blue;
   (c) determining the concentration of LMWH in the sample obtained from the manufacturing equipment by comparing its absorbance with the absorbances of a plurality of samples of control LMWH in aqueous solutions of known concentrations; and
   (d) determining the concentration of LMWH in the sample of obtained from the manufacturing equipment; and
   (e) optionally repeating steps (a)-(d) until the concentration of LMWH in the sample obtained from the manufacturing equipment is less than an acceptable residual concentration of LMWH.

The method can be carried out in accordance with the invention in any suitable assay container, such as, e.g., in a microtiter plate or a cuvette. Thus, the method carried out in accordance with the invention is accurate, quantitative, quick, easily performed, and amenable to high throughput.

DETAILED DESCRIPTION OF THE INVENTION

The invention provides a method of measuring the concentration of a test glycosaminoglycan anticoagulant in an aqueous solution of unknown concentration comprising:
   (a) assaying a sample containing the test glycosaminoglycan anticoagulant comprising (i) providing a sample containing the test glycosaminoglycan anticoagulant; (ii) reacting the sample with 1,9-dimethyl-methylene blue; and (iii) determining the absorbance of the sample after reaction with 1,9-dimethyl-methylene blue; and
   (b) determining the concentration of the sample containing the test glycosaminoglycan anticoagulant by comparing its absorbance with the absorbances of a plurality of samples of control glycosaminoglycan anticoagulant in aqueous solutions of known concentration.

The invention also provides a method of measuring the concentration of a test glycosaminoglycan anticoagulant, such as, e.g., a LMWH, in an aqueous solution comprising:
   (a) preparing a standard curve comprising (i) providing a plurality of samples of a control glycosaminoglycan anticoagulant in an aqueous solutions of known concentration, (ii) reacting the samples of known concentration with 1,9-dimethyl-methylene blue, (iii) determining the absorbance of the samples of known concentration after their reaction with 1,9-dimethyl-methylene blue;
   (b) assaying a sample containing the test glycosaminoglycan anticoagulant of unknown concentration in an aqueous solution comprising (i) providing a sample containing the test glycosaminoglycan anticoagulant of unknown concentration, (ii) reacting the sample of unknown concentration with 1,9-dimethyl-methylene blue, (iii) determining the absorbance of the sample of unknown concentration after reaction with 1,9-dimethyl-methylene blue; and
   (c) determining the concentration of the sample containing the test glycosaminoglycan anticoagulant of unknown concentration by comparing its absorbance with the absorbances of the standard curve samples of control glycosaminoglycan anticoagulant in an aqueous solutions of known concentration.

The absorbances of the control samples may be obtained prior to, during or after the determination of the absorbance of the sample of the test glycosaminoglycan anticoagulant. Thus, the comparison may be carried out, for example, using the absorbances of a plurality of historical control samples from prior experiments.

The method can be carried out in accordance with the invention in any suitable assay container, including, e.g., in the channel of a micro-electro-mechanical system ("MEMS device"), capillary tube, microtiter plate, cuvette or any other suitable container. Accordingly, absorbance at 656 nm can be determined in accordance with the invention in, e.g. without limitation, a spectrophotometer, colorimeter, coagulation analyzer or a microtiter plate reader.

The term "assaying" refers to determining or measuring an unknown concentration or, alternatively, confirming a presumed or purported concentration.

The term "unit of manufacturing equipment" refers to a machine, container and/or device, or group of machines, containers and/or devices for use in the preparation of glycosaminoglycan anticoagulants including, in particular, LMWHs. The unit of manufacturing equipment can include compounding equipment, filling equipment, or both.

The term "acceptable residual concentration of LMWH" refers to the concentration expected from the cleaning protocol used as determined by those of ordinary skill in the art or by governmental or non-governmental standard setting body or organization.

The term "cleaning protocol" refers to any suitable cleaning method hot water, steam, compressed air, surfactant solution, oxidized water solution, and combinations thereof.

The term "holding container" refers to all or part of a unit of manufacturing equipment that stores chemicals used in the generation of a drug product or the product.

The term "mixing container" refers to all or part of a unit of manufacturing equipment that mixes chemicals used in the generation of a drug product.

The term "reaction container" refers to all or part of a unit of manufacturing equipment in which a chemical reaction chemicals used in the generation of a drug product takes place.

The term "low flow conduit" refers to all or part of a unit of manufacturing equipment that conveys, with low throughput, chemicals used in the generation of a drug product or the product (e.g., an elbow).

The term "high flow conduit" refers to all or part of a unit of manufacturing equipment that conveys, with high throughput, chemicals used in the generation of a drug product or the product (e.g., a straight pipe).

The term "dispensing device" refers to all or part of a unit of manufacturing equipment that releases chemicals from the unit.

The standard curve of absorbances of samples having known concentrations of the LMWH is obtained by a process comprising: (a) preparing a plurality of samples of known LMWH concentration; (b) reacting the samples of known LMWH concentration with 1,9-dimethyl-methylene blue; (c) determining the absorbance of the samples of known LMWH concentration reacted with 1,9 dimethyl-methylene blue; and (d) graphing the absorbances obtained in (c) versus the known LMWH concentrations of the corresponding samples.

The term "graphing the absorbances" refers to graphing on paper and any other suitable mathematical method for determining the relationship between two variables, including but not limited to regression, interpolation, extrapolation, done manually or by a computer program.

For example, a standard curve may be generated by linear regression analysis performed on the absorbance of the samples of known concentration after their reaction with 1,9-dimethyl-methylene blue. Generally, the standard curve is generated using at least 3 controls of known glycosaminoglycan concentration, preferably at least 5 controls of known glycosaminoglycan concentration, more preferably at least 7 controls of known glycosaminoglycan concentration.

"Concentration" can be expressed, in accordance with the invention, in terms of any suitable units, including without limitation, molar, millimolar, micromolar, percent by weight or volume, mg/ml, or µg/ml.

Any suitable glycosaminoglycan anticoagulant can be used in the method of the present invention. Generally, the test glycosaminoglycan anticoagulant has a mean molecular weight of less than about 10,000 Daltons, preferably less than about 7,000 Daltons or even more preferably less than about 3,000 Daltons. Preferably, the glycosaminoglycan anticoagulant is a LMWH. Preferably, the LMWH is fondaparinux, ardeparin, bemiparin, dalteparin, enoxaparin, nadroparin, reviparin, tinzaparin or intimatan. Combinations of LMWHs may also be used. More preferably, the LMWH is fondaparinux (marketed as Arixtra® by GlaxoSmithKline), dalteparin (marketed as Fragmin® by Eisai) or enoxaparin (marketed as Lovenox® by Sanofi-Aventis). The LMWH may optionally be used in a salt folia such as, for example, the sodium salt. Alternatively, the test glycosaminoglycan anticoagulant used in accordance with the invention can be one or more oversulfated glycosaminoglycans.

Any suitable control or standard glycosaminoglycan can be used in accordance with the invention, including without limitation, chondroitin-4-sulfate, a LMWH Reference Standard from the European Directorate for the Quality of Medicines (EDQM) (e.g., EDQM Catalog Code: H0190000) or reference standard of a similar quality from an established standards setting organization. Typically, the reference standard for enoxaparin is 200 mg/vial and for dalteparin is 250 mg/vial.

Stock Standard Solutions (SSS) for use in accordance with the invention include, e.g., without limitation: (1) LMWH (EDQM Reference Standard) at 1 mg/ml; (2) a specific LMWH of known concentration; and (3) Chondroitin-4-Sulfate (C-4-S) at 100 µg/ml.

Suitable amounts of C-4-S or LMWH can be in the range of from about 0.5 µg to about 10 µg, preferably from about 0.7 µg to about 7 µg, more preferably from about 1 µg to about 5 µg. Test samples can be used in accordance with the invention include, without limitation, those in the range of from about 0.5 µg to about 10 µg, preferably from about 0.7 µg to about 7 µg, more preferably from about 1 µg to about 5 µg.

The volume for all standards and test samples can be, e.g. without limitation, adjusted to 200 µl with water, preferably 150 µl with water, more preferably 100 µl with water. The assay reaction can be done with a precise amount of 1,9-dimethyl-methylene blue (DMMB) reagent which is in the range of from about 1 to about 2 milliliters (mL) of DMMB reagent. The standards and test samples are mixed with this reagent for a precise time period which is at least 30 minutes at a precise temperature which is at least about 25° C.

It is desirable to isolate the glycosaminoglycan-DMMB complex from soluble materials, such as excess DMMB excess. This can be done, for example, by first preparing a DMMB solution in a formate buffer pH 3.0 containing 5% ethanol and 0.2 M guanidine hydrochloride.

Alternatively, the DMMB solution contains an amount of a buffer similar to formate, e.g. without limitation, sodium acetate or citrate phosphate, effective to stabilize the dye complex test solution and preclude precipitation of glycosaminoglycan. Preferably, the buffer used is sodium formate at a concentration of from about 0.05 M to about 0.25 M. Most preferably, about 0.2 M sodium formate buffer is employed. When done in accordance with the invention, the reaction between the DMMB and the glycosaminoglycan is complete after from about 3 seconds to about 60 minutes, preferably after from about 1 minute to about 40 minutes, most preferably after about 30 minutes, when the reaction is incubated at from about 20° C. to about 37° C., preferably at from about 22° C. to about 30° C., most preferably at about 25° C.

Ethanol at low pH (e.g., pH less than about 4.0, preferably pH less than about 3.0, more preferably pH less than about 2.5, most preferably pH less than about 2.0) is used for the exhaustive precipitation of the complex. Typically, the standards and test samples are then centrifuged at about 12,500 rpm and the resulting supernatant was decanted. One ml of a suitable resuspension reagent is added to each pellet, the pellet is resuspended and absorbance at 656 nm was measured with, e.g., a spectrophotometer. The resuspension reagent contains a chaotropic agent (e.g., guanidine, thiourea, isocyanate, urea or combinations thereof) in a suitable alcohol (e.g., propanol, isopropanol, methanol, ethanol or combinations thereof). This reagent is formulated to dissociate the glycosaminoglycan-dye complex and to enhance the absorption profile of the free dye.

If the absorbance readings, or "optical density" (OD) readings, at 656 nm, are greater than about 1.5, then the test sample should be diluted and re-assayed. Desirably five or ten-fold dilutions of the test sample are used. If the initial sample trial aliquots produced absorbance values of less than about 0.05 at 656 nm (following subtraction of the reagent blank value) then the test sample contains less than 0.2 μg glycosaminoglycan and the sample concentration should be considered before being re-assayed.

To determine standards and test samples net mean absorbance, the mean absorbance values of the blanks were subtracted from the mean absorbance values of the standards and test samples.

"Comparing absorbances" means establishing a mathematical relationship between the test samples absorbance value and the concentration based on the absorbances of the standard samples. This mathematical relationship can be established by any suitable method. For example, the mathematical relationship can be established by determining the position of the test absorbance on a manually drawn curve of standard sample blank-corrected absorbances versus the standard samples' known concentrations. Preferably, the mathematical relationship can be established using linear regression analysis, well known to those of ordinary skill in the art, based on the blank-corrected absorbance values of the standard samples.

Linear regression can be performed in any suitable way, including without limitation, the use of computer programs such as Microsoft Excel®. When historical controls are used as the basis of the comparison, typically the results from at least 10 historical controls of known glycosaminoglycan concentration, preferably from at least 25 historical controls of known glycosaminoglycan concentration, more preferably from at least 50 historical controls of known glycosaminoglycan concentration, most preferably from at least 100 historical controls should be used to establish the relationship.

An embodiment of the invention can be used, e.g., for "in-process testing." The concentration of enoxaparin before its addition in solution to, e.g., syringes can be determined using a method in accordance with the invention to verify that the solid form of enoxaparin dissolved to give the expected concentration. Another embodiment of the invention can be used to test "content-uniformity." For example, the concentration of enoxaparin in syringes can be determined before accelerated stability testing to confirm that the starting amounts of enoxaparin are uniform throughout the samples to be used in the study.

In another embodiment the invention provides a method for cleaning a unit of manufacturing equipment used in the preparation of low molecular weight heparin (LMWH) to establish that an acceptable residual concentration of LMWH has been obtained. Preferably, the present invention is applied to equipment used in the preparation of enoxaparin.

Figure 1:
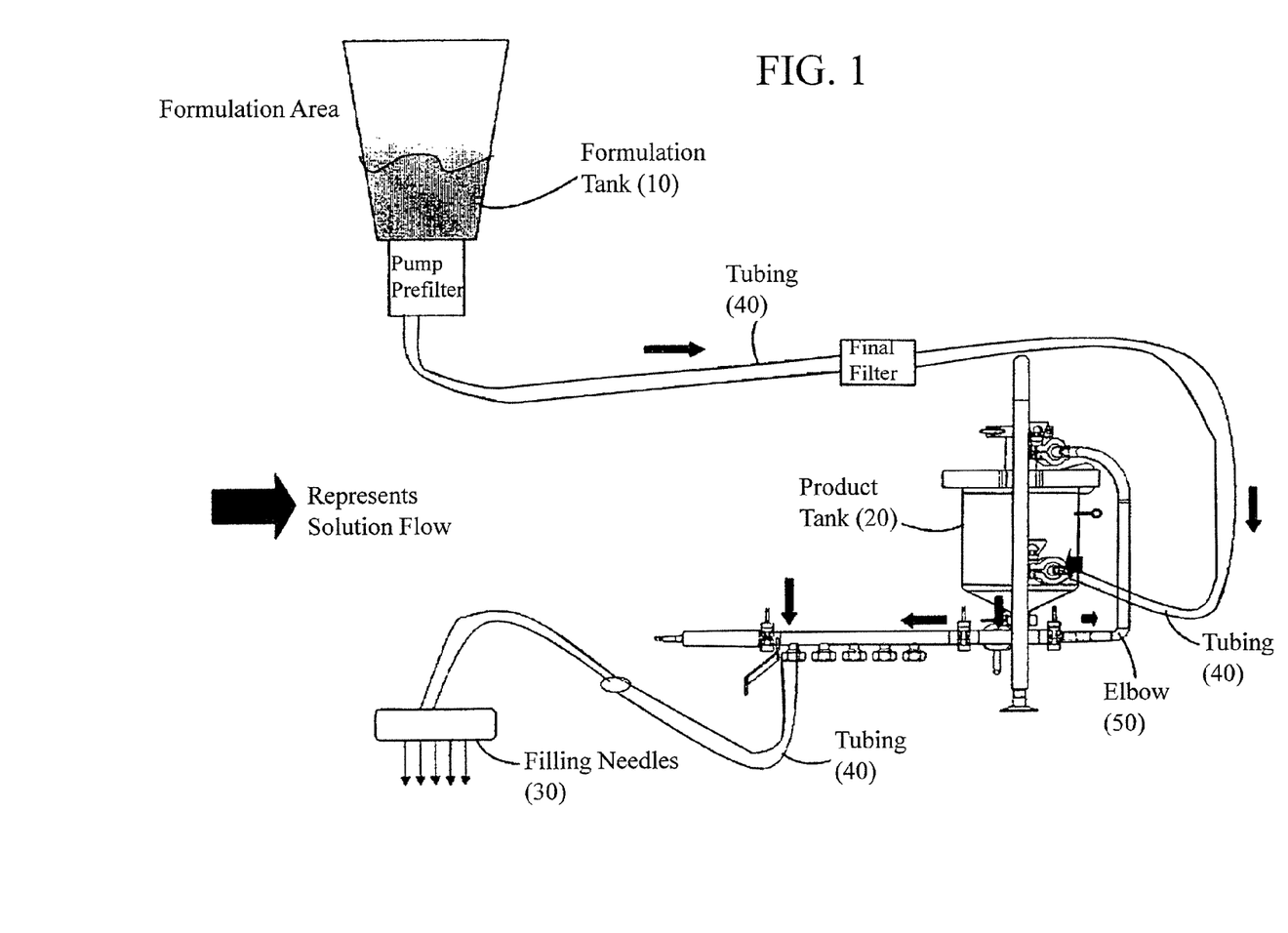
FIG. 1 is a schematic diagram of a unit of manufacturing equipment for producing LMWHs.

An example of a unit of manufacturing equipment that can be cleaned according to the present invention is illustrated in FIG. 1. The unit of manufacturing equipment may include a formulation tank 10, a product tank 20, filling needles 30, and tubing 40. These various components may be connected by suitable tubing. As discussed herein, the complete assembly of components that make up the unit of manufacturing equipment is referred to as the "equipment train." With respect to FIG. 1, the equipment train includes the formulation tank 10, product tank 20, filling needles 30, tubing 40 as well as all other components.

Any suitable cleaning protocol may be employed to wash the unit of manufacturing equipment. For example, purified water, hot water, steam, compressed air, surfactant solution, oxidized water solution, and combinations thereof may be used to wash the equipment. Any suitable volume of washing solution, e.g., 100 mL, preferably 200 mL, most preferably greater than 500 mL. The washing process can be repeated one or more times as necessary.

The sample or samples obtained from the unit of manufacturing equipment may be obtained from any suitable surface of the unit including, e.g., the surface of one or more of the following: holding container (e.g., tank), mixing container, reactor, mixing device (e.g., impeller and shaft), low flow conduit, high flow conduit, and dispensing device. With respect to unit of manufacturing equipment illustrated in FIG. 1, samples may be obtained from the formulation tank 10, product tank 20, filling needles 30, tubing 40, and/or elbow 50.

The sample may be obtained by any suitable method, including, e.g., swabbing, scrubbing, rinsing, scraping or wiping the surface of the unit of manufacturing equipment. Any suitable volume of rinsate may be used, for example, 5 mL, preferably 7 mL, more preferably 10 mL, and most preferably 12 mL.

The absorbance of the sample from the manufacturing equipment is obtained as discussed above by reacting the sample with 1,9-dimethyl-methylene blue and then determining the absorbance of the resulting sample. The concentration of LMWH in the sample is determined by comparing its absorbance with the absorbances of a plurality of samples of control LMWHs in aqueous solutions of known concentration. Preferably, the absorbance of the sample is compared to a standard curve of absorbances obtained from a plurality of samples having known concentrations of the LMWH. Based on the comparison of absorbances, the concentration of the LMWH in the sample obtained from the unit of manufacturing equipment can be determined.

The standard curve of absorbances of samples having known concentrations of the LMWH is obtained by a process comprising:

(a) preparing a plurality of samples of known LMWH concentration;

(b) reacting the samples of known LMWH concentration with 1,9-dimethyl-methylene blue;

(c) determining the absorbance of the samples of known LMWH concentration reacted with 1,9 dimethyl-methylene blue; and (d) graphing the absorbances obtaining in (c) versus the known LMWH concentrations of the corresponding samples The acceptable residual concentration of LMWH can be any suitable concentration such that the residual concentration does not adversely impact the use of the manufacturing equipment in the production of any pharmaceutical product including LMWHs or otherwise. Typically, a suitable LMWH concentration is less than about 7.8 micrograms per square inch of surface area. Alternatively, an acceptable residual concentration can be less than about 5.0 microgram per milliliter of sample, preferably less than about 2.5 micrograms per milliliter of sample, more preferably less than about 1.8 micrograms per milliliter of sample, and most preferably less than about 1.0 micrograms per milliliter of sample.

When the method of the invention is used for cleaning enoxaparin as illustrated in FIG. 1, the following concentrations of enoxaparin are acceptable:

TABLE 1

|  | Based on 80 L tank | Based on 10 L tank | Based on 1000 L tank |
|---|---|---|---|
| Equipment Train (4 in² swab) | 31.8 mcg/4 in² | 31.1 mcg/4 in² | 20.4 mcg/in² |
| Filling Needle (with 5 mL rinsate) | 0.986 mcg/mL | 0.963 mcg/mL | 0.62 mcg/mL |
| Elbow (with 25 mL rinsate) | 1.70 mcg/mL | 1.67 mcg/mL | 1.08 mcg/mL |
| With 2 mL rinse |  |  |  |
| Filling Needle | 2.46 mcg/mL | 2.41 mcg/mL | 1.55 mcg/mL |
| With 10 mL Rinse |  |  |  |
| Elbow | 4.26 mcg/mL | 4.17 mcg/mL | 2.70 mcg/mL |

If an acceptable residual concentration of LMWH is not obtained, the cleaning protocol on the unit of manufacturing equipment may be repeated one or more times. After each subsequent cleaning, the concentration of the LMWH is determined as described herein by determining the absorbance of a sample after its reaction with 1,9-dimethyl-methylene blue.

The following examples further illustrate the invention but, of course, should not be construed as in any way limiting its scope.

EXAMPLE 1

This example demonstrates the utility of the invention for determining the concentration of LMWHs.

Determinations of the concentrations of test LMWHs in aqueous solution were done in accordance with the invention using an exemplary assay system, the Blyscan™ Assay Kit (BioColor Ltd., Newtownabbey, Northern Ireland).

Stock Standard Solutions (SSS) were prepared including: (1) LMWH (EDQM) at 1 mg/ml; (2) LMWH (EDQM) at 0.04 mg/ml; and (3) Chondroitin-4-Sulfate (C-4-S) at 100 µg/ml.

Suitable volumes of C-4-S or LMWH SSS were transferred into duplicate 1.5 ml microfuge tubes to obtain a standard range of 1-5 µg. The test samples were prepared so as to obtain preparations containing in the range of 1-5 µg of unknown.

The volume for all standards and test samples were adjusted to 100 µl with water and 1 ml 1,9-dimethyl-methylene blue reagent was added. The standards and test samples were mixed with this reagent for 30 minutes at 25° C. The standards and test samples were then centrifuged at 10,000 rpm and the resulting supernatant was decanted. One milliliter of resuspension reagent was added to each pellet, the pellet was resuspended and absorbance at 656 nm was measured with a spectrophotometer. The absorbance at 656 nm of a blank containing only resuspension reagent was also measured.

To determine standards and test samples net mean absorbance, the mean absorbance values of the blanks were subtracted from the mean absorbance values of the standards and test samples. Concentrations were calculated according to the following equation:

$$Wi = Ai/m$$

where Wi is the weight of the ith component, Ai is the absorbance of the ith component, and m is the slope of the standard curve or the ratio of the slopes relative to C-4-S.

Linear regression analysis was used to construct a standard curve from the Blank-corrected absorbance values.

Figure 2:
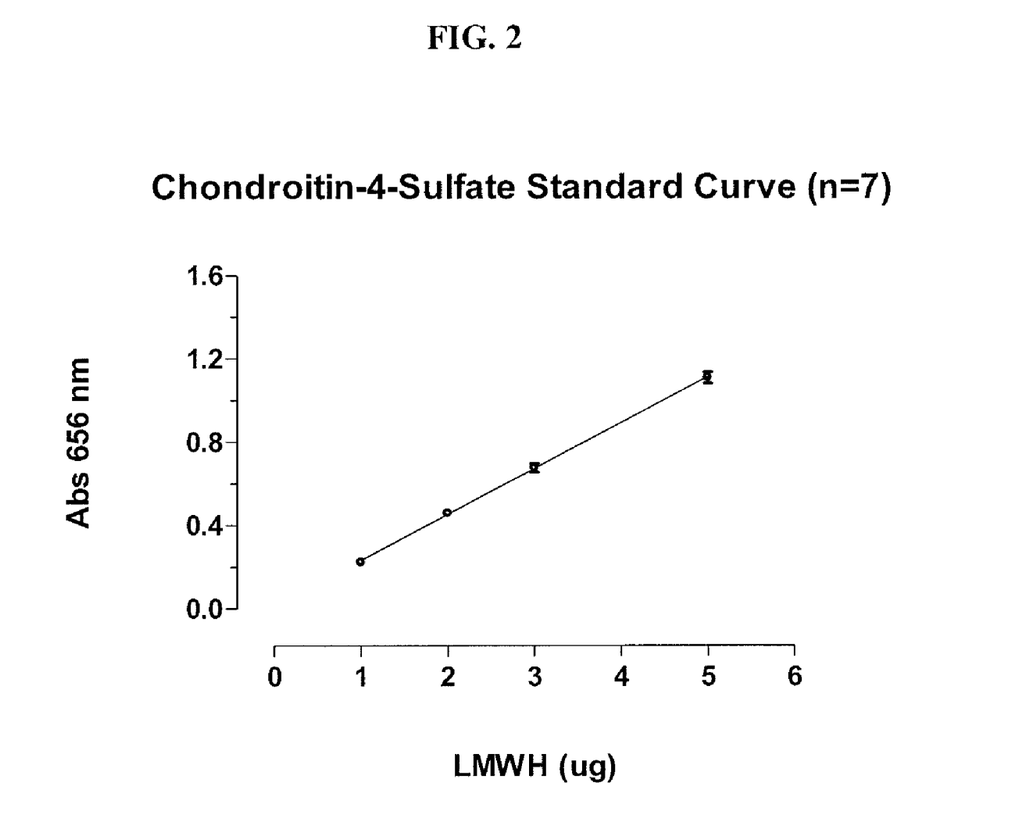
FIG. 2 depicts an exemplary standard curve generated in accordance with the invention using chondroitin-4-sulfate (C-4-S).

The utility of any concentration assay is enhanced by a linear dose-response at relevant concentrations of suitable standards and the assay targets. An exemplary standard curve generated using C-4-S is shown in FIG. 2. The statistics for this curve are given in Table 2.

TABLE 2

| Equation | Slope | $\hat{r}2$ |
|---|---|---|
| y = 0.2368x + 0.0159 | 0.2368 | 0.9999 |
| y = 0.2168x + 0.0281 | 0.2168 | 0.9956 |
| y = 0.2292x + 0.0242 | 0.2292 | 0.9994 |
| y = 0.2359x + 0.0093 | 0.2359 | 0.9995 |
| y = 0.2027x + 0.0147 | 0.2027 | 0.9998 |
| y = 0.2105x − 0.0151 | 0.2105 | 0.9994 |
| y = 0.2115x − 0.002 | 0.2115 | 1 |
| Average | 0.2205 | 0.9991 |
| StDev | 0.013 | 0.002 |
| % RSD (n = 7) | 6.1 | 0.2 |

Theses data, having an average Correlation Coefficient ($r^2$) of 0.999, indicate that there is a linear dose-response relationship for the C-4-S concentration range examined.

Figure 3:
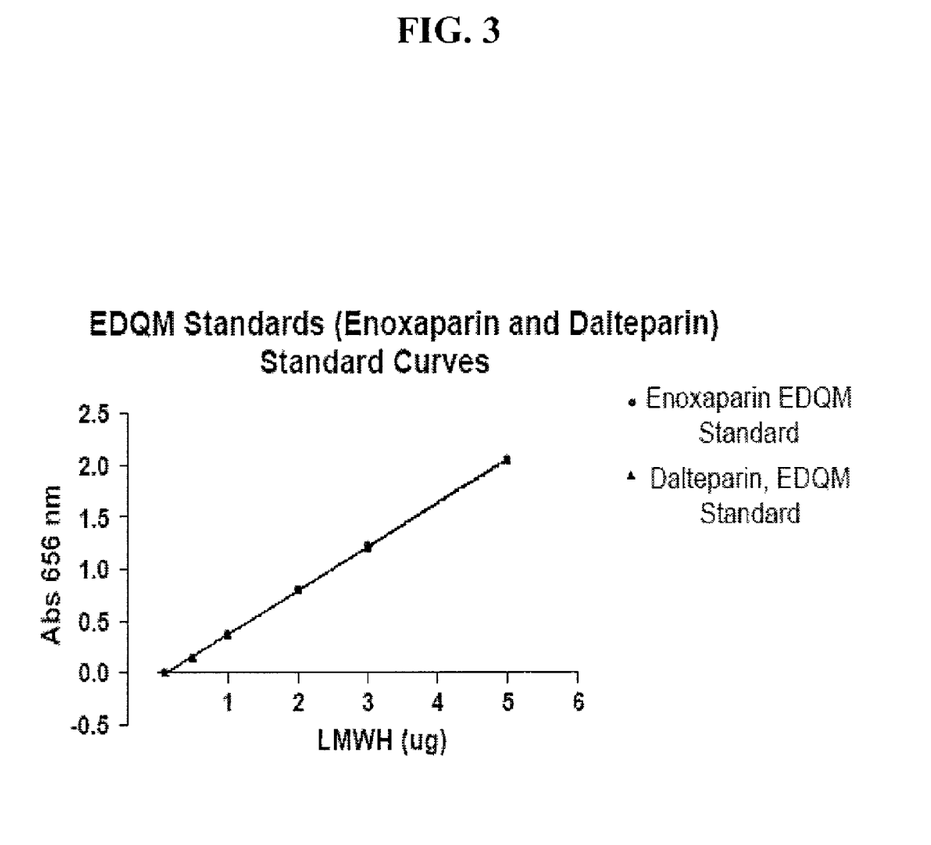
FIG. 3 depicts an exemplary standard curve generated in accordance with the invention generated with enoxaparin and dalteparin (reference standards supplied by the European Directorate for the Quality of Medicines)

The LMWHs enoxaparin and dalteparin also produce a linear dose-response relationship (FIG. 3). A statistical analysis of the results yields correlation coefficients for enoxaparin and dalteparin of 0.9998 and 0.9998, respectively, indicating that linear dose-responses are present.

Table 3 further illustrates that the method performed in accordance with the invention produces a linear dose-response. The linearity response were studied for the LMWHs enoxaparin (EDQM), dalteparin (EDQM), Lovenox (marketed by Aventis), Fragmin® (marketed by Pharmacia), and Arixtra® (marketed by Alchemia), as well as the standard chondroitin-4-sulfate (BioColor, Ltd.) for concentrations ranging from <1 µg/ml to 5 µg/ml. A comparison of the slopes and the correlation coefficients are shown in Table 3, (*n=4, n=1, *n=7). All samples had correlation coefficients of at least 0.98 indicating that linear dose-response relationships are present.

TABLE 3

| Sample | Slope | Correlation Coefficient |
|---|---|---|
| *enoxaparin (EDQM): | 0.420 +/− 0.029 | $r^2 = 0.9994$ |
| *dalteparin (EDQM): | 0.418 +/− 0.026 | $r^2 = 0.9990$ |
| **Arixtra ® | 0.512 +/− 0.029 | $r^2 = 0.9996$ |
| **Lovenox ® | 0.439 +/− 0.010 | $r^2 = 0.9990$ |
| **Fragmin ® | 0.425 +/− 0.018 | $r^2 = 0.9995$ |
| ***C-4-S | 0.238 +/− 0.002 | $r^2 = 0.9803$ |

Figure 4A:
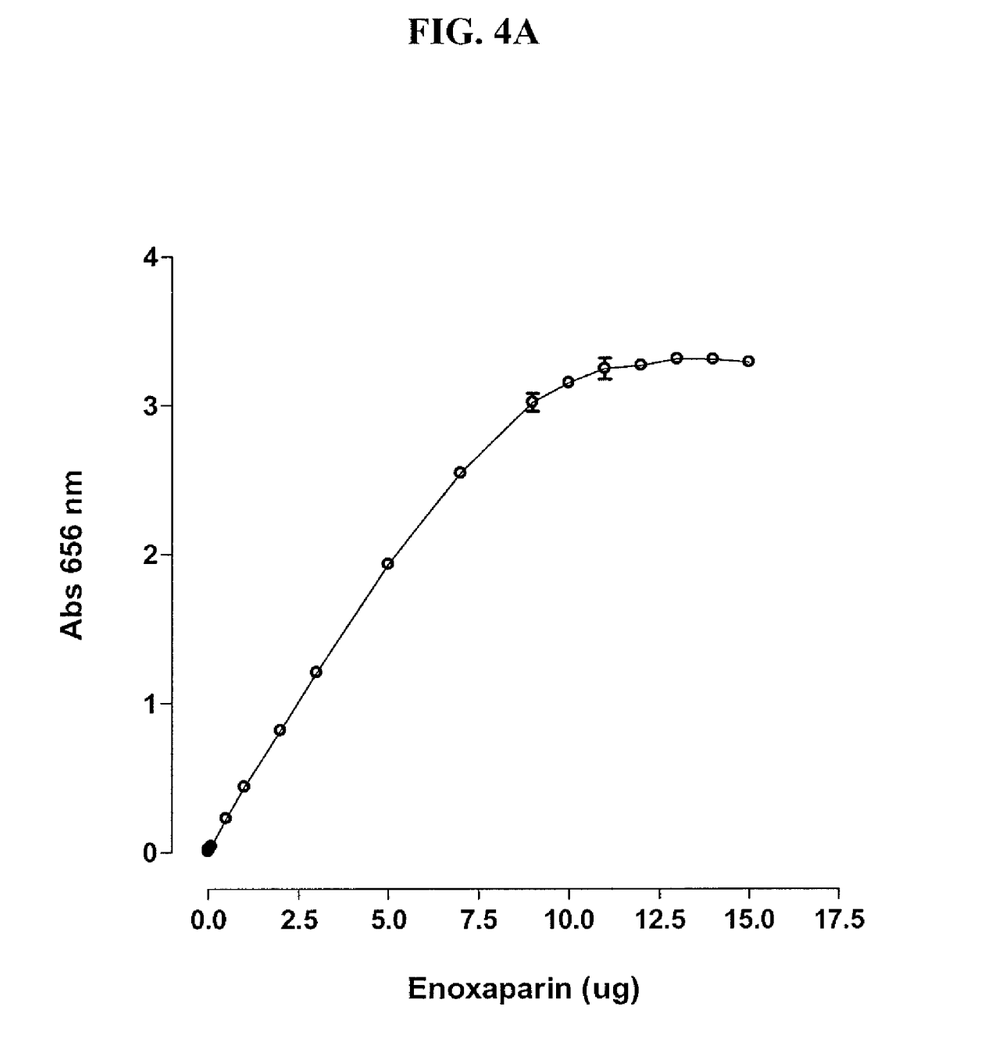
FIG. 4A depicts saturation of the enoxaparin dose-response curve.
Figure 4B:
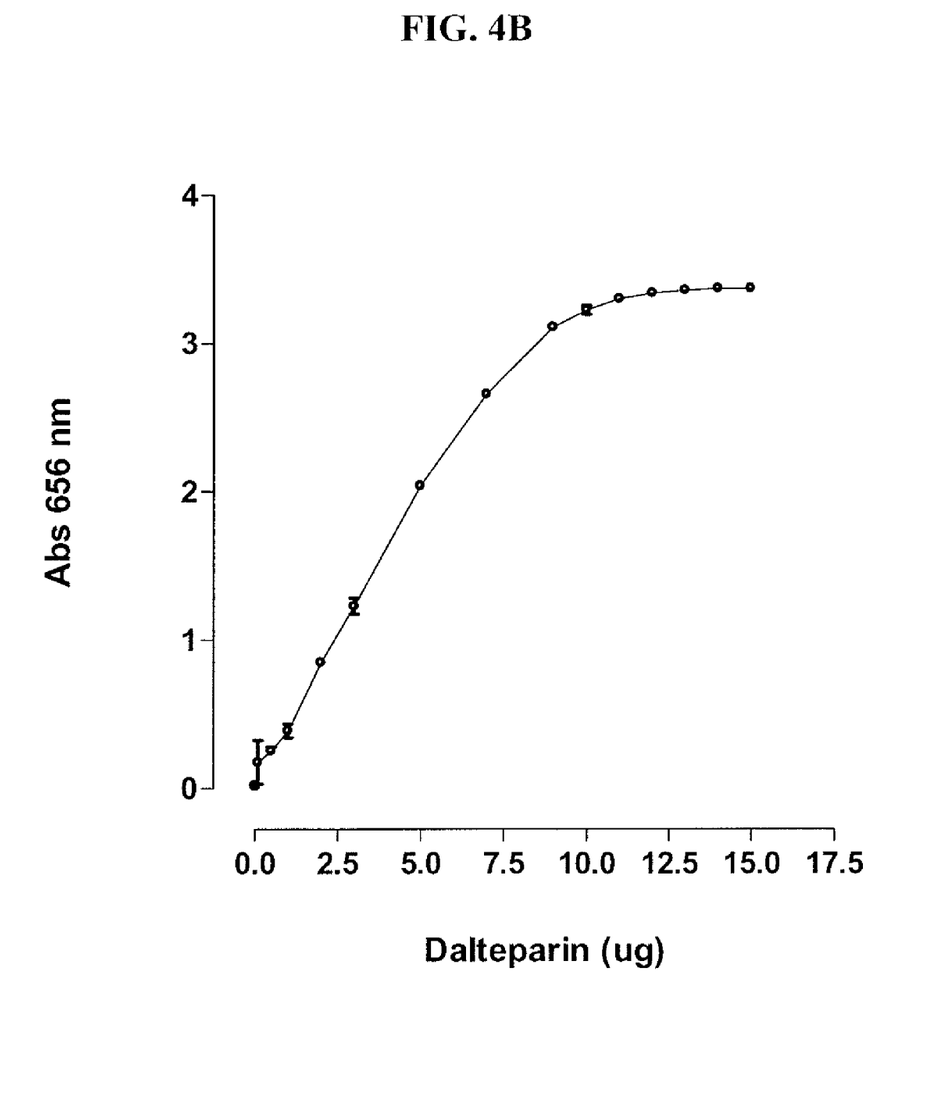
FIG. 4B depicts saturation of the dalteparin dose-response curve.

However, as shown by FIG. 4, the assay is saturated at high LMWH concentrations. The dose-response curves for enoxaparin (FIG. 4A) and dalteparin (FIG. 4B) both plateau at about 10 µg/ml.

EXAMPLE 2

Figure 5:
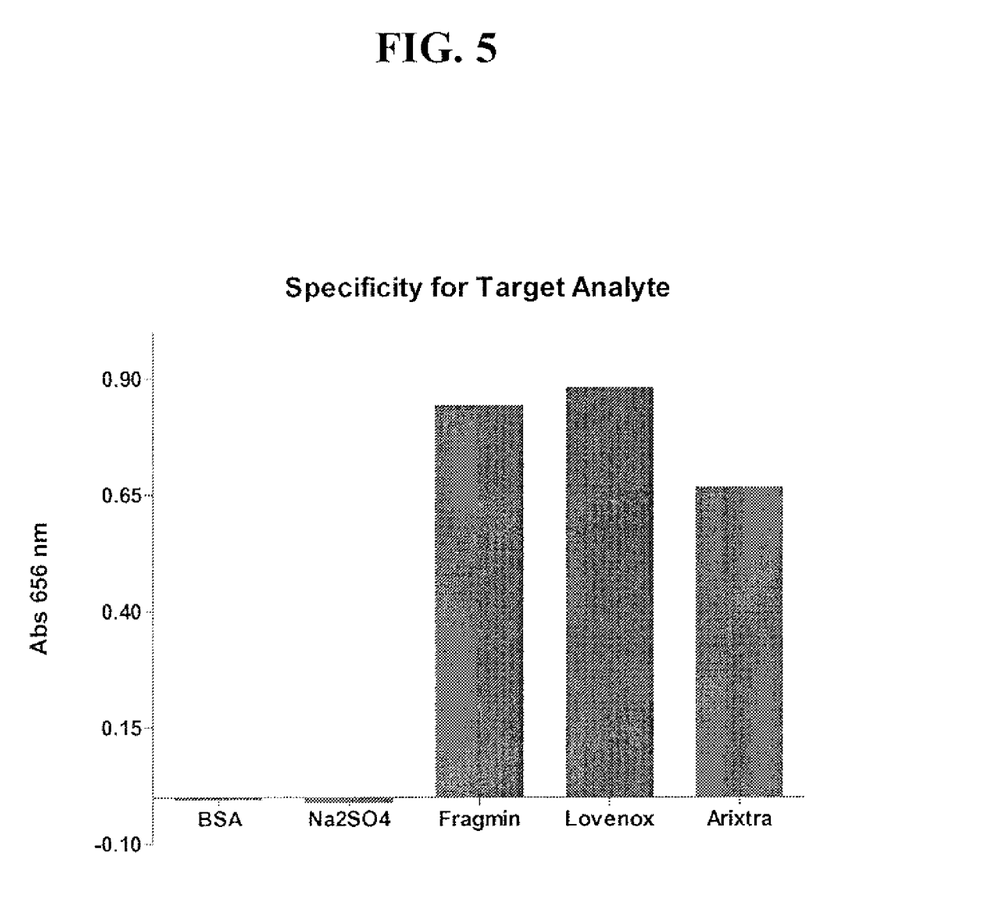
FIG. 5 depicts the results obtained analyzing LMWHs and non-anticoagulants.

This example demonstrates the inventive method's specificity and the absence of potential interference from a non-anticoagulant likely to be in an assay mix. Approximately equal concentrations of the LMWHs Fragmin®, Lovenox®, and Arixtra® and the non-anticoagulant exemplary serum protein BSA were assayed in accordance with the invention (Sodium Sulfate is a negative-control). BSA is often used as a product stabilizer. As shown in FIG. 5 the inventive method distinguished, with substantially different OD readings, the LMWHs from non-anticoagulant protein BSA.

EXAMPLE 3

Figure 6:
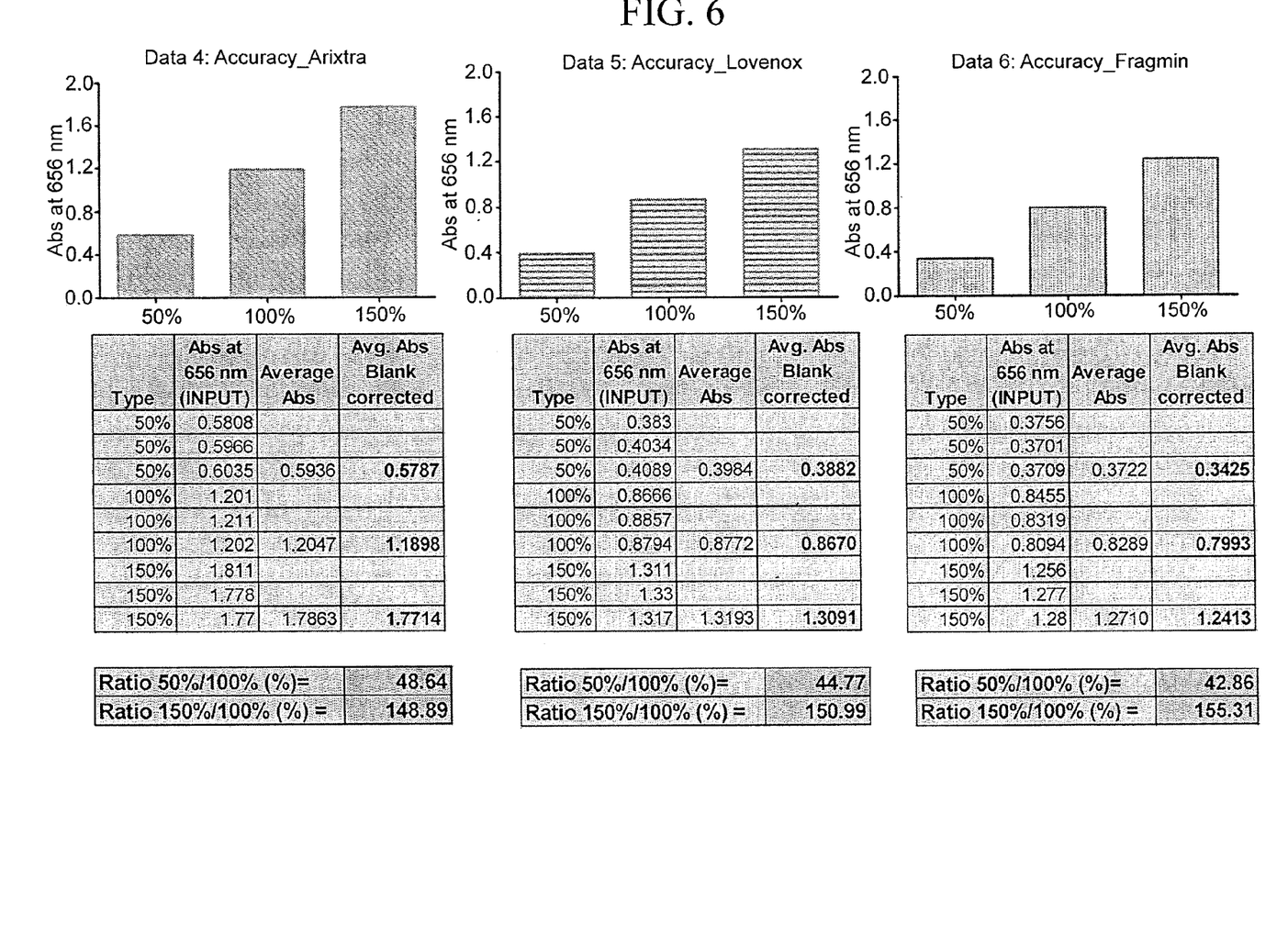
FIG. 6 depicts the results generated by inventive method for Arixtra®, Lovenox®, and Fragmin® solutions of various known concentrations.

This example demonstrates the accuracy of the method at different concentrations of three LMWHs. The method was evaluated by determining the percent recovery of the "spiked" solutions of Arixtra®, Lovenox®, and Fragmin® added at 50%:100%:150% of claim (FIG. 6.). The method yielded results that were within 10% of the expected result, indicating a high degree of accuracy

EXAMPLE 4

This example demonstrates the intra-day variability of a single analyst using the inventive method on a single day. The intra-day variability for each test sample was found to be less than 5%. This example also demonstrates the minor inter-analyst variability and reproducibility of the inventive method between two analysts on different days. The method was performed as detailed in Example 1 using 2 μg samples of Arixtra®, Lovenox®, and Fragmin® and the precision values were found to be less than 10%

The results are show in Tables 4-6.

TABLE 4

Arixtra (2 ug)

| | | Run 1 | Run 2 | Run 3 |
|---|---|---|---|---|
| 1 | | 1.158 | 0.982 | 1.219 |
| 2 | | 1.086 | 1.056 | 1.237 |
| 3 | | 1.161 | 1.022 | 1.233 |
| 4 | | 1.162 | 1.033 | 1.233 |
| 5 | | 1.145 | 1.062 | 1.199 |
| 6 | | 1.143 | 1.020 | 1.230 |
| Mean | (n = 6) | 1.1425 | 1.0292 | 1.2252 |
| StDev | (n = 6) | 0.0288 | 0.0289 | 0.0142 |
| % RSD | (n = 6) | 2.5 | 2.8 | 1.2 |
| Mean | (n = 18) | | 1.1323 | |
| StDev | (n = 18) | | 0.0859 | |
| % RSD | (n = 18) | | 7.6 | |

TABLE 5

Lovenox (2 ug)

| | | Run 1 | Run 2 | Run 3 |
|---|---|---|---|---|
| 1 | | 0.785 | 0.789 | 0.814 |
| 2 | | 0.790 | 0.781 | 0.827 |
| 3 | | 0.787 | 0.794 | 0.827 |
| 4 | | 0.783 | 0.780 | 0.813 |
| 5 | | 0.740 | 0.802 | 0.822 |
| 6 | | 0.807 | 0.793 | 0.817 |
| Mean | (n = 6) | 0.7820 | 0.7898 | 0.8200 |
| StDev | (n = 6) | 0.0223 | 0.0084 | 0.0063 |
| % RSD | (n = 6) | 2.9 | 1.1 | 0.8 |
| Mean | (n = 18) | | 0.7973 | |

TABLE 5-continued

Lovenox (2 ug)

| | | Run 1 | Run 2 | Run 3 |
|---|---|---|---|---|
| StDev | (n = 18) | | 0.0215 | |
| % RSD | (n = 18) | | 2.7 | |

TABLE 6

Fragmin(2 ug)

| | | Run 1 | Run 2 | Run 3 |
|---|---|---|---|---|
| 1 | | 0.908 | 0.804 | 0.975 |
| 2 | | 0.909 | 0.784 | 0.910 |
| 3 | | 0.914 | 0.812 | 0.954 |
| 4 | | 0.918 | 0.807 | 0.978 |
| 5 | | 0.906 | 0.784 | 0.969 |
| 6 | | 0.936 | 0.800 | 0.981 |
| Mean | (n = 6) | 0.9152 | 0.7985 | 0.9612 |
| StDev | (n = 6) | 0.0111 | 0.0119 | 0.0268 |
| % RSD | (n = 6) | 1.2 | 1.5 | 2.8 |
| Mean | (n = 18) | | 0.8916 | |
| StDev | (n = 18) | | 0.0725 | |
| % RSD | (n = 18) | | 8.1 | |

Relative Standard Deviations (% RSD) ranged from only 2.7% to 8.1%, demonstrating the adaptability of the inventive method to multiple users and the methods reproducibility over multiple runs.

EXAMPLE 4

This example demonstrates the utility of the present invention in determining the commercial anticoagulants.

Commercial doses anticoagulant with labeled concentrations where obtained and their concentrations determined using the methods of the present invention and C-4-S to generate the standard curve. A commercial dose of Arixtra® in a syringe with the labeled concentration of 10 mg/0.8 ml was analyzed. The mean concentration determined by the repeated analysis with the method of the invention (n=6) was 10.3 mg/0.8 ml or 100.3% of the claimed concentration. A commercial dose of Fragmin® in a syringe with the labeled concentration of 48 mg/0.3 ml was also analyzed. The mean concentration determined by the repeated analysis with the method of the present invention (n=6) was 51.8 mg/0.3 ml or 107% of the claimed concentration. In addition, a commercial dose of Lovenox® in a syringe with the labeled concentration of 100 mg/ml was analyzed. The mean concentration determined by the repeated analysis with the method of the present invention (n=6) was 103.9 mg/ml or 103.9% of the claimed concentration.

Further, commercial doses of the anticoagulants enoxaparin and dalteparin with labeled concentrations were obtained and their concentrations determined using the methods of the present invention. enoxaparin and dalteparin EDQM standards, respectively, were used to generate the standard curves. The dose of enoxaparin, labeled as "100 mg/ml," was measured using the method of the present invention and found to have a concentration of 99.6+/−0.8 mg/ml. The dose of dalteparin, indicated on the label to have a concentration of 48 mg/0.3 ml, was measured using the method of the present invention and found to have a concentration of 51.4+/−0.4 mg/ml.

EXAMPLE 5

This example demonstrates the adaptability of the method to batch processing. It is desirable for an assay to allow for batch processing Batch processing is facilitated by the ability to stabilize samples for final testing at a later time.

Figure 7:
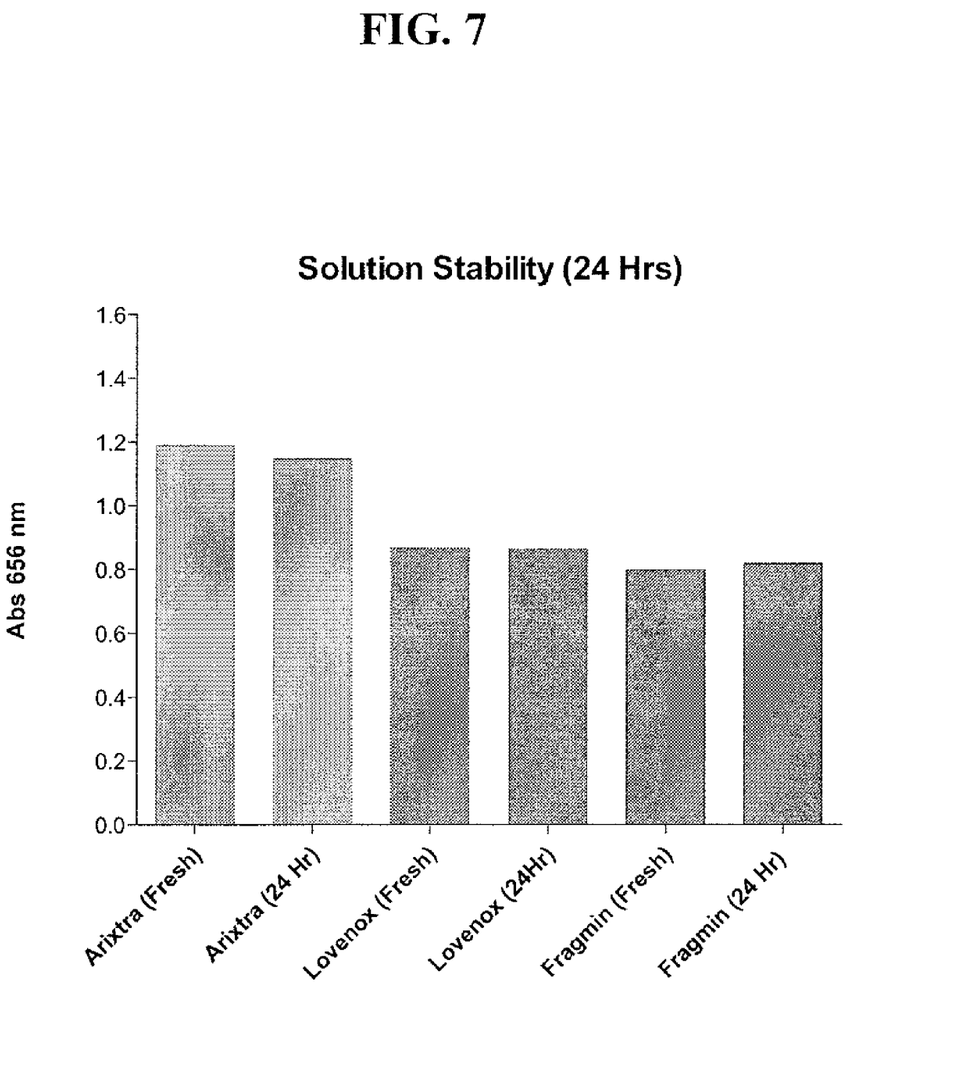
FIG. 7 depicts solution stability at 24 hrs for Arixtra®, Lovenox®, and Fragmin®

FIG. 7 shows the results of the method when the OD is read immediately as compared to a reading after a 24 hour "hold." The results show that there is no effect from the 24 hour hold. Accordingly, the method provides for the stabilization of either sample or test solution stored prior to batch assay runs (e.g., OD readings).

Collectively, Examples 1-5, inter alia, show that the method of the present invention has utility with various anticoagulants and different standard reagents.

EXAMPLE 6

This example demonstrates that there are decreases in LMWH:dye binding associated with changes in sulfation content, molecular weight and bioactivity. While not desiring to be bound by any theory, these results are consistent with the inventive method functioning through the methylene blue reaction.

TABLE 7

| NaOH | Control | 0.1N NaOH | 1.0N |
|---|---|---|---|
| LMWH Assay (% of Control) | 100% | 73% | 20% |
| Desulfation (ppm) | 1.13 +/− 0.4 | 43.2 +/− 2.6 | 160.6 +/− 3.2 |
| Molecular Weight (% of control) | 100% | 89% | 78% |
| Anti Factor Xa (% of Control) | 100% | 82% | 7% |

EXAMPLE 7

This example demonstrates the application of the present invention to cleaning manufacturing equipment used in the preparation of a low molecular weight heparin, specifically enoxaparin, to obtain an acceptable residual concentration of enoxaparin.

Following the use of a unit of manufacturing equipment to produce enoxaparin, a suitable cleaning protocol was completed on the equipment. A swab assay was performed to determine the amount of enoxaparin recoverable by swabbing the stainless steel equipment train. The cleaning protocol is designed to obtain an enoxaparin concentration below the maximum allowable limit of 31.1 µg/4 in$^2$.

First a sample swab was prepared according to the following steps: (1) a 0.622 mg/ml solution of enoxaparin was prepared; (2) 50 µl of the solution was spread evenly on a stainless steel coupon such that the coupon contained 31.1 µg of enoxaparin; (3) The coupon was dried and swabbed with a pre-wet (in water) swab; (4) the swab was transferred to 10 mL of water and vortexed; and (5) 1 ml was transferred into 1.5 ml microcentrifuge tube, dried in a speedvac, and brought up in 100 µl of water. The sample, thus prepared, contained an amount of enoxaparin equal to 3.11 µg. A control was prepared according to the following procedure: (1) a 3.11 mg/ml solution of enoxaparin was prepared; and (2) 1.0 ml was transferred to a 1.5 ml microcentrifuge tube, dried down, and brought up in 100 µl of water. The control, thus prepared, also contained an amount of enoxaparin equal to 3.11 µg.

Figure 8A:
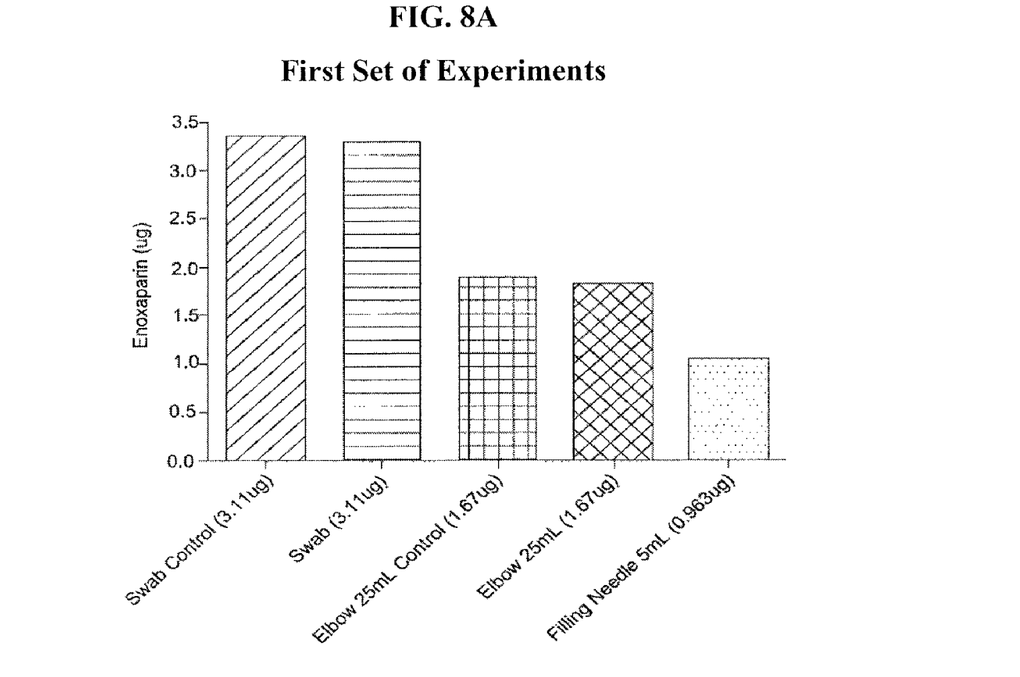
FIG. 8A depicts the first set of results obtained from an analysis of residual LMWH concentrations following the cleaning of a unit of manufacturing equipment pursuant to a cleaning protocol.
Figure 8B:
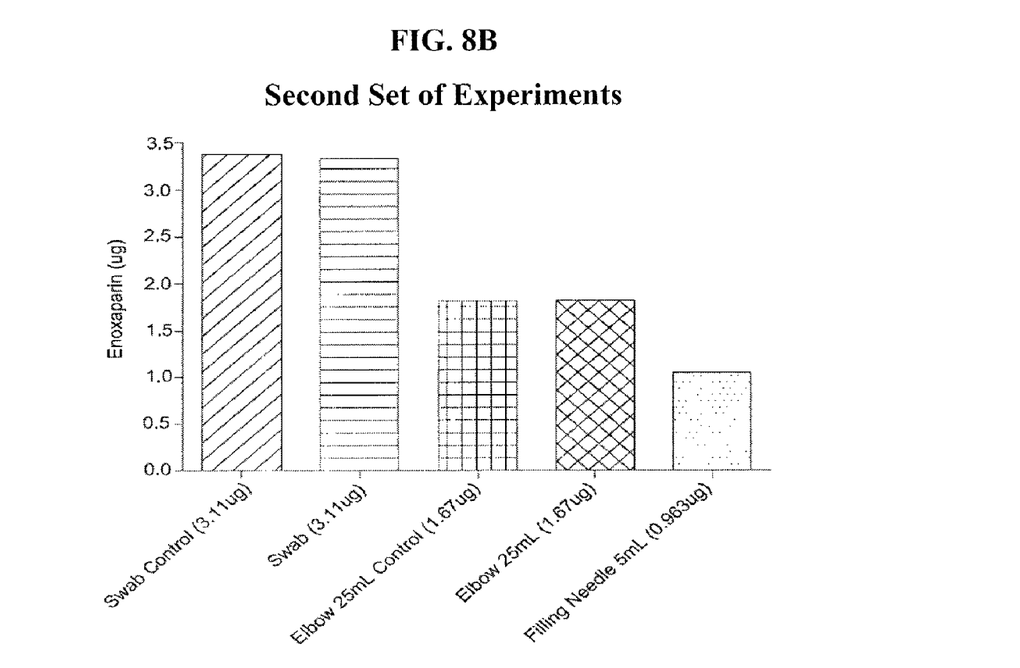
FIG. 8B depicts the second set of results obtained from an analysis of residual LMWH concentrations following the cleaning of a unit of manufacturing equipment pursuant to a cleaning protocol.

The sample swab and the control swab were analyzed according to the present invention. 3.11 µg enoxaparin was detected, confirming that 31.1 µg was present in the full 10 ml sample. This assay indicates that an amount of enoxaparin equal to the allowable limit was detectable by swabbing stainless steel and assaying according to the present invention. The results are represented in the first two columns of the graph in FIG. 8A. An identical assay was performed on a second day and the results were the same (see first two columns of FIG. 8B).

A similar assay was performed to demonstrate the amount of rinsate recoverable from a 25 ml rinsate of a stainless steel elbow (see FIG. 1) with a maximum allowable concentration of 1.67 µg/ml. A sample was prepared according to the following steps: (1) A 25 ml solution having an enoxaparin concentration of 1.67 µg/ml was prepared; (2) 1 ml was transferred to a 1.5 ml microcentrifuge tube, dried in a speedvac and brought up in 100 µl water. The sample, thusly prepared contained 1.67 µg enoxaparin. A control was prepared in a 1.5 ml microcentrifuge tube containing 1.67 µg enoxaparin in 100 µl water. The two tubes were assayed according to the present invention. 1.67 µg enoxaparin was detected in both. This assay demonstrates that the present invention can detect an amount of enoxaparin equal to the allowable level in a 25 ml rinsate. The results are represented in the second two columns of the graph in FIG. 8A. An identical assay was performed on a second day and the results were the same (see second two columns of FIG. 8B).

Finally, an assay was performed to demonstrate the amount of enoxaparin recoverable from 5 ml sample from a stainless steel filling needle (see FIG. 1) with a maximum allowable amount of 0.963 µg/ml. A 5 ml solution was prepared with a concentration of 0.963 µg/ml. 1.0 ml was transferred to a 1.5 ml microcentrifuge tube, dried down and brought up in 100 µl water. This sample was assayed according to the present invention and 0.963 µg enoxaparin was detected. This indicates that the present invention can detect an amount of enoxaparin equal to the maximum allowable level in a 5 ml rinsate. The results are represented in the last column of the graph in FIG. 8A. An identical assay was performed on a second day and the results were the same (see last column of FIG. 8B).

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method of cleaning a unit of manufacturing equipment used in the preparation of heparin to obtain an acceptable residual concentration of heparin comprising:
   (a) subjecting the unit of manufacturing equipment to a cleaning protocol;
   (b) obtaining the absorbance of a sample obtained from the manufacturing equipment comprising:
      (i) collecting a sample from the manufacturing equipment;
      (ii) reacting the sample with 1,9-dimethyl-methylene blue; and
      (iii) determining the absorbance of the sample reacted with 1,9 dimethyl methylene blue;
   (c) determining the concentration of heparin in the sample obtained from the manufacturing equipment by comparing its absorbance with the absorbances of a plurality of samples of control heparin in aqueous solutions of known concentrations; and
   (d) optionally repeating steps (a)-(c) until the concentration of heparin in the sample obtained from the manufacturing equipment is less than an acceptable residual concentration of heparin.

2. The method of claim 1, wherein in step (c) the absorbance of the heparin sample is compared to a standard curve of absorbances obtained from a plurality of samples having known concentrations of the heparin.

3. The method of claim 2, wherein the standard curve of absorbances of samples having known concentrations of the heparin is obtained by a process comprising:
   (a) preparing a plurality of samples of known heparin concentration;
   (b) reacting the samples of known heparin concentration with 1,9-dimethyl-methylene blue;
   (c) determining the absorbance of the samples of known heparin concentration reacted with 1,9 dimethyl-methylene blue; and
   (d) graphing the absorbances obtained in step (c) versus the known heparin concentrations of the corresponding samples.

4. The method of claim 1, wherein a plurality of samples are obtained from the manufacturing equipment.

5. The method of claim 4, wherein the plurality of samples obtained from the unit of manufacturing equipment are obtained from the surface of one or more of a holding container, a mixing container, a reaction container, a low flow conduit, a high flow conduit, and a dispensing device.

6. The method of claim 1, wherein the absorbances of the sample and the samples of known concentration are determined in a microtiter plate or a cuvette.

7. The method of claim 1, wherein the sample from the manufacturing equipment is obtained by swabbing, scrubbing, rinsing, scraping or wiping a surface of the unit of manufacturing equipment.

8. The method of claim 1, wherein the acceptable residual concentration of heparin is less than about 7.8 micrograms per square inch of surface area.

9. The method of claim 1, wherein the acceptable residual concentration of heparin is less than about 1.0 micrograms per milliliter of sample.

10. The method of claim 1, wherein the acceptable residual concentration of heparin is less than about 1.8 micrograms per milliliter of sample.

* * * * *